US006440711B1

(12) United States Patent
Davé

(10) Patent No.: US 6,440,711 B1
(45) Date of Patent: Aug. 27, 2002

(54) DEHYDROGENASE ENZYMATIC SYNTHESIS OF METHANOL

(75) Inventor: Bakul Davé, Carbondale, IL (US)

(73) Assignee: Board of Trustees Southern Illinois University, The, Carbondale, IL (US)

( * ) Notice: Subject to any disclaimer, the term of this patent is extended or adjusted under 35 U.S.C. 154(b) by 0 days.

(21) Appl. No.: 09/733,345

(22) Filed: Dec. 8, 2000

(51) Int. Cl.⁷ .................................................. C12P 7/04
(52) U.S. Cl. ...................................................... 435/157
(58) Field of Search ............................... 435/157, 155, 435/160, 161

(56) References Cited

U.S. PATENT DOCUMENTS

| | | |
|---|---|---|
| 4,512,855 A | 4/1985 | Mazur |
| 4,830,903 A | 5/1989 | Levy |
| 5,128,013 A | 7/1992 | Helms |
| 5,200,334 A | 4/1993 | Dunn et al. |
| 6,066,269 A | 5/2000 | Wei et al. |

OTHER PUBLICATIONS

Obert et al., J. MA. Chem. Soc., 121(51), 1999, pp. 12192–12193.*
Obert et al., Chemical abstracts: 1999:93219 of the Bood of Abstracts, 217th ACS National Meeting, Anaheim, Calif, Mar. 21–25, 1999.*
Kuwabata et al., J. Am. Chem. Soc., 116(12), 1994, pp. 5437–5443.*
Dave, Chemical Abstracts: 1999:93054 of the Book of Abstracts, 217th ACS National Meeting, Anaheim, Calif., Mar. 21–25, 1999.*
S. Cosnier, Biosensors and Bioelectronics, vol. 14, *Biomolecule immobilization on electrode surfaces by entrapment or attachment to electrochemically polymerized films. A review*, pp. 443–456, 1999.
Dunahay et al., Biochimica et Biophysica Acta, vol. 764, *Structural Biochemical and Biophysical Characterization of Four Oxygen–Evolving Photosystem II Preparations from Spinach*, pp. 179–193, 1984.
Ghindilis et al., Electroanalysis, vol. 9, No. 9, *Enzyme–Catalyzed Direct Electron Transfer: Fundamentals and Analytical Applications*, pp. 661–674, 1997.
Habermueller et al., Fresenius J. Anal. Chem, vol. 366, *Electron–transfer mechanisms in amperometric biosensors*, pp. 560–568, 2000.
Hummel, Publication Unknown, *Large–scale applications of NAD(P)–dependent oxidoreductases: recent developments*, 6 pp., date unknown.
Kieselbach et al., The Journal of Biological Chemistry, vol. 273, No. 12, *The Thylakoid Lumen of Chloroplasts*, pp. 6710–6716, Mar. 20, 1998.
Kuwabata et al, J. American Chemical Society, vol. 116, No. 12, *Electrochemical Conversion of Carbon Dioxide to Methanol with the Assistance of Formate Dehydrogenase and Methanol Dehydrogenase as Biocatalysts*, pp. 5437–5443, 1994.
Mandler et al., J. Chem. Soc, Perkin Trans. II, *Photochemical Fixation of Carbon Dioxide: Enzymic Photosynthesis of Malic, Aspartic, Isocitric, and Formic Acids in Artificial Media*, pp. 997–1003, 1988.
Obert et al., Journal of the American Chemical Society, vol. 121, No. 51, *Enzymatic Conversion of Carbon Dioxide to Methanol: Enhanced Methanol Production in Silica Sol–Gel Matrices*, pp. 12192–12193, 1999.
Parkinson et al., Publication Unknown, *Photoelectrochemical pumping of enzymatic $CO_2$ reduction*, 2 pp. 1984.
Ruschig et al., Eur. J. Biochem., vol. 70, *$CO_2$ Reduction to Formate by NADH Catalysed by Formate Dehydrogenase from Pseudomonas oxalaticus*, pp. 325–330, 1976.

* cited by examiner

Primary Examiner—Samuel Barts
Assistant Examiner—Elvis O. Price

(57) ABSTRACT

A method for conversion of carbon dioxide to methanol comprises contacting formate dehydrogenase enzymes, formaldehyde dehydrogenase enzymes and additional dehydrogenase enzymes selected from the group consisting of alcohol dehydrogenase enzymes and methanol dehydrogenase enzymes with the carbon dioxide in the presence of a terminal electron donor to produce the methanol. The intermediate reduction reactions are assisted by retaining the enzymes in a microporous matrix.

24 Claims, 2 Drawing Sheets

DEHYDROGENASE ENZYMATIC SYNTHESIS OF METHANOL

BACKGROUND OF THE INVENTION

(1) Field of the Invention

The present invention relates to chemical reductions catalyzed by dehydrogenase enzymes and more particularly to the implementation of such reductions in the synthesis of methanol.

(2) Description of the Related Art

Methanol is used in a wide range of applications. Among such applications may be noted its use in the production of formaldehyde, in automotive anti-freeze, in a variety of chemical syntheses, as a general solvent, as an aviation fuel (for water injection), as a denaturant for ethyl alcohol, and as a dehydrator for natural gas. Conventional techniques for the production of methanol include high-pressure catalytic synthesis from carbon monoxide and hydrogen, partial oxidation of natural gas hydrocarbons, and purification of pyroligneous acid resulting from destructive distillation of wood.

Various techniques for synthesizing methanol from carbon dioxide are also known. As noted in Enzymatic Conversion of Carbon Dioxide to Methanol: Enhanced Methanol Production in Silica Sol-Gel Matrices, J. Amer. Chem. Soc. 1999, 121, 12192–12193 (published on the World Wide Web on Dec. 9, 1999), partial hydrogenation of carbon dioxide has been carried out by means of heterogeneous catalysis, electro-catalysis, and photocatalysis, with oxide-based catalysts being used predominantly for industrial fixation of carbon dioxide.

Derivation of methanol from carbon dioxide has several obvious advantages. For example, carbon dioxide is plentiful, readily available (indeed, omnipresent), and extremely inexpensive, to say the least. In addition, whereas use of many resources may lead to undesirable depletion of that resource, rising levels of carbon dioxide have been associated with what has been referred to as the "greenhouse" effect, which has been theorized to be a contributing factor to global warming. Thus, moderate removal of carbon dioxide from the atmosphere is viewed as beneficial rather than detrimental.

However, conventional methods for synthesizing methanol from carbon dioxide also suffer from certain drawbacks. Such drawbacks include inefficiencies, costs, high energy consumption, and the need for special equipment adapted for high temperature or highly corrosive environments. For example, one common commercial method of methanol synthesis is by reduction of carbon dioxide in the presence of oxide catalysts. However, this synthesis produces partially reduced species as by-products, thereby not only creating impurities but also resulting in limited conversion efficiency. Moreover, the process is carried out at high temperatures, requiring special equipment for accommodating and maintaining such temperatures as well as high energy input.

Various other procedures for reduction of carbon dioxide by enzyme-catalyzed reactions also have been described, but such processes either have not been directed to methanol production or involve various drawbacks. Thus, for example, in $CO_2$ Reduction to Formate by NADH Catalysed by Formate Dehydrogenase from Pseudomonas oxalaticus, Ruschig et al., Eur. J. Biochem. 70, 325–330 (1976), a direct reduction of carbon dioxide by formate dehydrogenase using substrate amounts of NADH is disclosed. The carbon dioxide is reported to have been reduced to formate via carbonate formation in a reaction requiring strict anaerobic conditions to prevent oxygen-induced oxidation of the NADH.

Parkinson and Weaver also describe the production of formate via the formate dehydrogenase catalyzed reduction of carbon dioxide. Photoelectrochemical Pumping of Enzymatic $CO_2$ Reduction, Nature 309, 148 (1984). In their process, Parkinson and Weaver report that a 150 watt tungsten/halogen lamp generated electrons from the semiconductor indium phosphide to reduce methyl viologen ($MV^{2+}$), which they state mediated the enzyme linked reduction of carbon dioxide to formate. Parkinson and Weaver state that an electrochemical reaction was used to reduce $MV^{2+}$.

Mandler and Willner discuss relaying photoinduced electrons generated by the $(Ru(bpy)_3)^{2+}/MV^{2+}$ system to an electron transfer molecule such as 2-mercaptoethanol or cystine. Photochemical Fixation of Carbon Dioxide: Enzymic Photosynthesis of Malic, Aspartic, Isocitric, and Formic Acids in Artificial Media, J. Chemical Soc., Perkin Trans., 997 (1988). According to Mandler and Willner, the 2-mercaptoethanol so energized reduced NADP+to generate NADPH, which mediated the enzyme-induced carboxylation of pyruvate to malate. Likewise, Mandler and Willner show that cysteine is capable of donating electrons in the formate dehydrogenase-induced reaction of $CO_2$ to formate. Mandler and Willner note that the formate dehydrogenase activity is problematic because it decays rapidly upon exposure to light, and postulate that since the decarboxylation of formic acid is so energetically favorable, NADH is too weak a reducer to enable efficient production of formate.

Kuwabata et al. describe the sequential reduction of carbon dioxide to methanol by use of formate dehydrogenase and methanol dehydrogenase enzymes, wherein electrons are generated electrochemically and either pyrroloquinolinequinone (PQQ) or $MV^{2+}$ is used as the electron carrier. Thus, the Kuwabata et al. technique is an electrolytic process that requires everything essential to such processes, including an elecrolytic bath, electrodes, and electrical current input, and also requires use of PPQ or $MV^{2+}$. Moreover, Kuwabata et al. report that the electrolysis had to be carried out in the dark to maintain the durability of the formate dehydrogenase enzyme.

Accordingly, a new technique for synthesis of methanol, and especially conversion of carbon dioxide to methanol, that alleviates such drawbacks is desired. In particular, a low temperature, highly efficient technique for production of methanol from carbon dioxide is desired.

SUMMARY OF THE INVENTION

Briefly, therefore, the present invention is directed to a novel method for conversion of carbon dioxide to methanol. According to the method, a combination of formate dehydrogenase enzymes, formaldehyde dehydrogenase enzymes and either alcohol dehydrogenase enzymes or methanol dehydrogenase enzymes is contacted with the carbon dioxide in the presence of a terminal electron donor to produce the methanol. Preferably, the enzymes are fixed in a microporous matrix such as a sol-gel and the terminal electron donor is a cofactor of the enzymes, such as reduced nicotinamide adenine dinucleotide (which can also donate hydrogen ions to the reductions as well) matrix. In a most preferred embodiment, the invention also contemplates a mechanism for regeneration of the terminal electron donor for reuse.

This synthesis is made up of a series of synthesis steps, from carbon dioxide to formate, from formate to formaldehyde and from formaldehyde to methanol. Thus, the present invention is also directed to each of such steps and sub-combinations of steps, which are assisted by retaining the enzymes in a microporous matrix.

Accordingly, the present invention is also directed to a novel method comprising reduction of formaldehyde to methanol by alcohol dehydrogenase catalysis, to a novel method comprising reduction of formate to formaldehyde by formaldehyde dehydrogenase catalysis, to a novel method comprising reduction of carbon dioxide to formate by formate dehydrogenase catalysis, to a novel method comprising reduction of carbon dioxide to formaldehyde by a combination of formate dehydrogenase catalysis and formaldehyde dehydrogenase catalysis, and to a method comprising reduction of formate to methanol by a combination of formaldehyde dehydrogenase catalysis and alcohol dehydrogenase catalysis.

Among the several advantages found to be achieved by the present invention, therefore, may be noted the provision of a method for synthesis of methanol from carbon dioxide at low temperature; the provision of such method that is energy efficient; the provision of such method that yields high conversion rates; the provision of such method that avoids the need for special equipment adapted to high temperature or highly corrosive environments; and the provision of related methods associated with the intermediary steps of such synthesis.

DETAILED DESCRIPTION OF THE PREFERRED EMBODIMENTS

Figure 1:
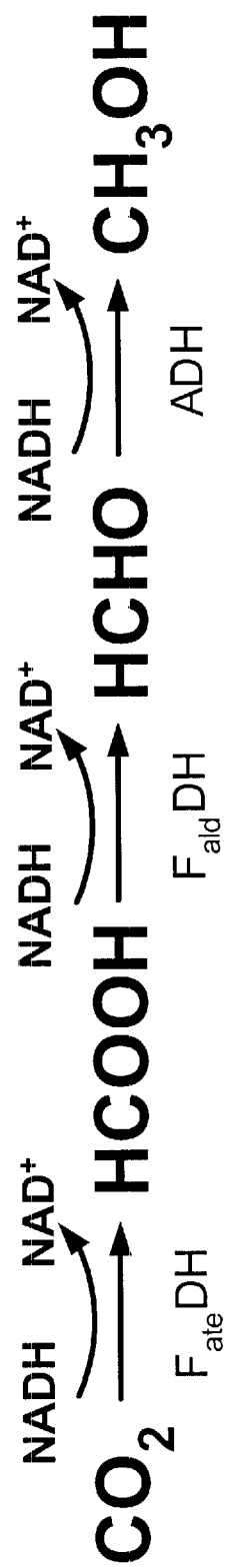
FIG. 1 is a schematic illustration of the series of reduction reactions of this invention.

In accordance with the present invention, it has been discovered that by contacting a combination of dehydrogenase enzymes with carbon dioxide, a low temperature, high-yield reduction of the carbon dioxide to methanol may be carried out without special equipment designed for high temperatures or corrosive environments. Moreover, it has been found that this process is highly selective, resulting in high yield of methanol and little if any formation of undesirable by-products. This discovery is particularly surprising in view of the fact that the presence of the dehydrogenase enzymes employed in the subject reduction are known under conventional conditions to induce the opposite reaction, from methanol to carbon dioxide. However, it now has been found that by entrapping the enzymes within a matrix of micropores (i.e., very small pores)—especially, nano-pores on the order of billionths of meters in diameter—and particularly when driven by the presence of an abundance of donative electrons, for instance from an excess of the reduced form of a cofactor of the enzymes (such as nicotinamide adenine dinucleotide (NADH)) relative to the unreduced form (such as nicotinamide adenine dinucleotide ($AND^+$)), the equilibrium of the reaction can be shifted so that the tendency toward oxidation can be reversed, causing the reaction to proceed as a reduction of carbon dioxide to methanol. Although the inventor does not wish to be bound to any particular theory, he believes that the physical constraints of the small volume pores results in localized areas of relative reactant concentrations that adjust the stoichiometry at the reaction sites such that the equilibrium of the reaction favor reduction rather than oxidation.

In addition, it also has been found that the reduced form of the cofactor can be regenerated, recycled and re-used repeatedly. In other words, after the reduced form of the cofactor is oxidized by donating an electron to the dehydrogenase catalyzed reduction scheme of carbon dioxide to methanol, the reduced form of the cofactor may be regenerated from the form resulting from the oxidation, thereby allowing repeated re-use of a single dose of the cofactor. In fact, it has been found that the reduced cofactor serving as the electron donor can be regenerated and reused not just a few times, but at least many thousands of times. As a result, the method of this invention provides a surprisingly practical, low-cost, low energy consumption and efficient mechanism for converting carbon dioxide to methanol.

In short, according to the process of the present invention, a matrix containing a certain combination of dehydrogenase enzymes may be contacted with carbon dioxide to induce an ordered series of reduction reactions catalyzed by those enzymes ultimately to produce methanol. In practice, atmospheric carbon dioxide from any source, even atmosph may simply be bubbled through water containing a porous matrix that contains the enzymes entrapped in its pores. The water or matrix may contain several other components as well. Among the potential additional components may be noted several that are particularly desirable; namely, a terminal electron donor, which donates electrons to the reduction reactions, and a mechanism for regeneration of the electron donor for further electron donation. Each reduction step in the reaction scheme from carbon dioxide to methanol also consumes two hydrogen ions (protons) and so requires a source for such ions. In the embodiment of this invention that incorporates regeneration of the electron donor, the aqueous system may also include a mechanism for such regeneration.

The Matrix

The matrix within the enzymes are entrapped is, as noted above, a microporous, even nano-porous, structure capable of retaining the enzymes within the pores or interstices, but such that the enzymes also may be exposed to carbon dioxide transported (such as by bubbling) to or through the matrix. The matrix may be in the form of small particles or a powder (perhaps as the result of grinding) and suspended in the medium (e.g., water) in which the series of reduction reactions takes place. As will be explained below in the section discussing regeneration of the terminal electron donor, a particularly advantageous technique for such regeneration involves photo-regeneration. Therefore, because photo-regeneration relies on transmission of light through the matrix (or suspension of matrix particles), it is desirable in such case that the matrix be transparent.

The matrix may be made up of an inorganic solid such as an oxide, zeolite, meso-porous silicates, extended networks or layered materials. However, it has been found that sol-gel glasses are especially well suited to the subject process and so are particularly desirable matrix materials. The sol-gel process is a well-known technique involving the transition of a solution system from a liquid "sol" into a solid "gel" phase. Sols usually are prepared from a precursor such as an inorganic metal salt, a metal alkoxide or another metal organic compound. Preferably, the sol-gel glass useful in the subject invention is based on a silica precursor, such as those of the type $(OR)_4Si$, $RSi(OR)_3$, $RSi(OR)_2$, or $(OR)_3Si$-spacer-$Si(OR)_3$, wherein R is an alkyl, alkenyl, alkynyl, or aryl group, and the spacer unit comprises an organic unit, an inorganic unit, or a combination thereof. Although alkoxides or silicon are preferred, other metal oxides, such as those prepared by adding methanol, ethanol, isopropanol or other similar alcohols to the oxides of metals or non-metals such as aluminum, titanium, zirconium, niobium, hafnium, chromium, vanadium, tungsten, molybdenum, iron, tin, phosphorus, sodium, calcium, and boron, or combinations thereof, are candidates for precursors of the sol-gels of this invention. Nevertheless, tetramethylorthosilicate (TMOS) has been found to be a particularly useful precursor, and tetraethylorthosilicate (TEOS) and other active silicon compounds are preferred as well.

The precursor is subjected to a series of hydrolysis and polymerization reactions to form the "sol"—a colloidal suspension. Thin films can be deposited on a substrate such as by spin-coating or dip-coating, if so desired. Upon casting the "sol" in a mold, a "wet gel" is formed. The wet gel can be dried and heated until a dense material forms. However, if the liquid in a wet gel is extracted under a supercritical condition, a highly porous and extremely low-density material called an "aerogel" is formed. The resulting porous material is referred to as a "sol-gel glass." The average pore diameter in sol-gel glass typically ranges from 2 nm to 200 nm. The pores are interconnected and may be doped with almost any gas, liquid or solid.

The Enzymes

A combination of formate dehydrogenase ($F_{ate}DH$), formaldehyde dehydrogenase ($F_{ald}DH$), and alcohol dehydrogenase (ADH) enzymes has been found to be an especially effective combination of enzymes for catalyzing the ordered series of reductions, although it is believed that methanol dehydrogenase enzymes may be substituted for the alcohol dehydrogenase enzymes. The series of reduction reactions catalyzed by the enzymes has been found to proceed as follows. First, the formate dehydrogenase enzyme (e.g., E.C. 1.2.1.2, E.C. 1.2.1.43, or E.C. 1.2.2.3) induces a formate-catalyzed reduction of the carbon dioxide to formate. The formaldehyde dehydrogenase enzyme (e.g., E.C. 1.2.1.46) then catalyzes the reduction of the formate to formaldehyde. And the alcohol dehydrogenase enzyme (e.g., E.C. 1.1.1.1, E.C. 1.1.1.2, E.C. 1.1.1.71, or E.C. 1.1.99.8) then catalyzes the reduction of the formaldehyde to methanol. Of course, variations of these enzymes, and even mutant variations, that maintain the described catalytic functionality may be employed in place of any or all of these enzymes. It is therefore contemplated that such site-specific variants may be employed in place of the preferred enzymes without departing from the scope of this invention and discussion herein of the noted dehydrogenase enzymes is intended to encompass such variants as well.

Incorporation of the Enzymes in the Matrix

In the subject invention, the matrix is doped with the combination of enzymes discussed above. U.S. Pat. No. 5,200,334 to Dunn et al., incorporated herein by reference, describes a sol-gel process for the preparation of porous glass structures having active biological material such as protein entrapped therein, and notes that encapsulated or entrapped enzymes are used a micro-catalysts. Although the patent nowhere discloses or suggests the use of dehydrogenase enzymes, or particularly those dehydrogenase enzymes identified above, according to the present invention, the enzymes employed in this invention may be encapsulated into a sol-gel glass by the procedure described in U.S. Pat. No. 5,200,334. It has been found that use of enzymes trapped in a sol-gel matrix is three-to-four times more efficient at converting carbon dioxide to methanol than is the use of a mere solution of the enzymes.

The Terminal Electron Donor

As can be seen from the reaction scheme illustrated in FIG. 1, each of the reduction steps in the reaction scheme from carbon dioxide to methanol consumes an electron that must be donated from some source. However, if a free electron is provided, it may be introduced at any of a number of sites on the enzymes, resulting in undesirable side reactions. Therefore, for the aforementioned reactions to proceed as described, a mechanism to deliver the electron to the appropriate sites on the enzymes is desired. Thus, it is preferred that such a mechanism for donating electrons, such as a carrier that delivers the electron to the enzymes site-specifically, be included with the matrix (or water) as well. Cofactors of the enzymes provide such site-specific delivery and so are the preferred terminal electron donors. It has been found that reduced nicotinamide adenine dinucleotide (NADH) is especially well-suited to act as a terminal electron donor for each of the three reduction reactions. Thus, the overall synthesis may be shown schematically as in FIG. 1.

As noted above, the conventional direction of the series of reduction reactions carried out in this invention is actually the reverse of that carried out herein; that is, conventionally, the reactions tend to oxidation, which would result formation of carbon dioxide from methanol. However, it has been found that the thermodynamics of the reactions can be shifted so that the reverse reactions (that is, the reductions) are favored if the reduced cofactor is present in great excess of that called for by the stoichiometry of the oxidation reactions. As can be seen from FIG. 1 for the case of NADH, the stiochiometry calls for three moles of NADH for conversion of one mole of carbon dioxide to one mole of methanol. Thus, where the electron donor is NADH, for example, the reactions herein should be carried out in the presence of about 3,000 moles of NADH per mole carbon dioxide converted. Viewing it differently, it can be seen also from FIG. 1, that the reactions scheme yields three moles of $NAD^+$ per mole of carbon dioxide converted, and so the ratio of NADH to $NAD^+$ should be maintained on the order of 1,000 or more.

The Hydrogen Ion Donor

Although each reduction reaction in the overall scheme of this invention consumes two hydrogen ions, it is not necessary that the method include addition of a separate hydrogen ion donor for that sole and specific purpose. The hydrogen ions consumed in each of the reduction reactions may be derived from another additive (such as an acid), or from some other mechanism for supplying the ions but, alternatively, they may be derived from the water itself if the process of the subject invention is carried out in an aqueous system, from the terminal electron donor. If they are derived from the water, it may be preferred that the extraction of the hydrogen ion be accompanied by some other process to generate the ions or to compensate for the ramifications of the extraction. In other words, the continual removal of hydrogen ions from the water might increase the pH thereof, requiring—at least at some point—adjustment downward of the pH, such as by the addition or incorporation of a buffer or acid.

Generation of the hydrogen ions from the water may be carried out, for example, electrochemically, by addition of hydrogen gas, or by conversion of the water to oxygen gas. The conversion of water to oxygen gas may be accomplished, for example, photosynthetically, as will be discussed below with respect to regeneration of the electron donor. In that case, as will be discussed below, the hydrogen ions consumed in the reduction reactions may be supplied by the terminal electron donor, and the photosynthetic reaction may in turn serve to replenish the hydrogen ions to the terminal electron donor rather than the photosynthetic reaction supplying the hydrogen ions directly to the reduction reactions.

Regeneration of the Terminal Electron Donor and/or Hydrogen Ion Donor

As noted above, NADH has been found to be an excellent terminal electron donor and hydrogen ion donor in the process of this invention. However, NADH is relatively expensive. Therefore, it is desirable that if NADH is used, that the NADH be regenerated so that it can be recycled for repeated use. Surprisingly, it has been found not that only can the NADH indeed be regenerated from the $NAD^+$, but that it can be regenerated simply and "automatically" without a need for any additional steps that would involve, for example, removal of the $NAD^+$ from the reaction vessel, extra treatment and return to the reaction vessel and without any significant interference with the reduction reactions of this invention. In particular, it has been discovered that photosystem II (PSII) preparations, which contain chlorophyll and an $O_2$-evolving complex, can be extracted from green plants such as spinach and by simply adding the extracted PSII preparation to the reaction vessel—or to the matrix itself—and carrying out the reactions in the presence of light, the NADH can be regenerated and recycled automatically and continuously. Techniques for extraction of green plant PSII are well known. See, for example, Structural, Biochemical and Biophysical Characterization of Four Oxygen-Evolving Photosystem II Preparations from Spinach, T. Dunahay et al., Biochemica et Biophysica Acta, 764 (1984) 179–193.

Figure 2:
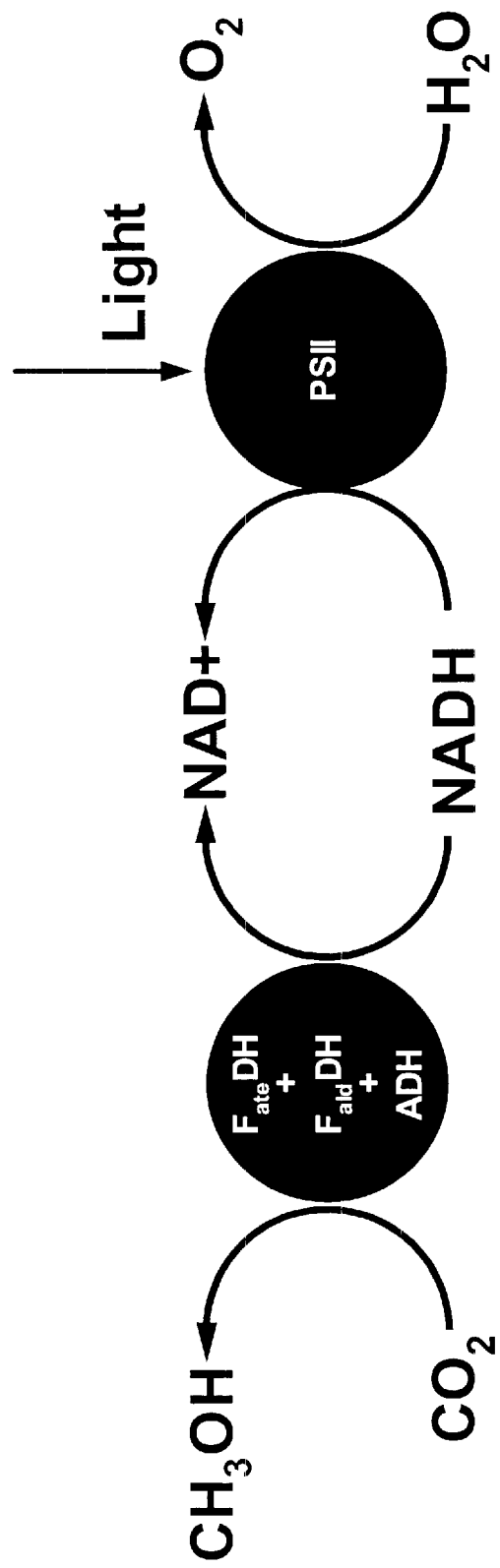
FIG. 2 is a schematic illustration of the the reduction of this invention from carbon dioxide to methanol, with regeneration and recycling of NADH.

Thus, upon extraction and incorporation of the PSII preparations into the reduction system of this invention and exposure of the PSII preparations to light the PSII preparations seem to use the $NAD^+$ as an electron-acceptor in place of the acceptor quinone of green plants. As a result, the PSII preparation photo-oxidizes the water in the system to oxygen ($O_2$), releasing hydrogen ions and electrons and thereby converting the $NAD^+$ back to NADH. See FIG. 2 for a schematic representation. According to the overall reaction, therefore, carbon dioxide, water and light are converted to methanol and oxygen. The reaction scheme has been found to run—apparently—indefinitely on the initial doses of the enzyme-containing matrix, NADH and PSII, requiring only carbon dioxide, water and light as input flows thereafter, and producing oxygen and methanol. Thus, the process closely mimics natural photosynthesis wherein photo-generated electrons produced from the oxidation of water synthesize hydrocarbons from carbon dioxide. The reactions with NADH regeneration and recycling have been carried out with green plant PSII, but it is believed that bacteria photosystem can be used in similar manner as well.

The extracted photosystem preparation may be incorporated into the reaction scheme of this invention by soaking the matrix in a suspension of the extracted photosystem preparation so that it diffuses through the matrix, adding the extracted photosystem preparation directly to the matrix-containing mixture for carrying out the process of this invention, or both. Because the photosystem reaction is activated by exposure to light, it is advantageous for the matrix to be transparent, so that the light can be transmittal without undue interference to the photosystem preparation.

Other alternatives for regeneration of the electron donor, hydrogen ion donor or both, and particularly, NADH, are available as well and will be readily apparent to those of ordinary skill in the art upon reading this specification, based on the recognition that what is required is a method for producing or introducing electrons and hydrogen ions. For example, hydrogen gas may be bubbling through the system, thereby effecting the reduction $NAD^+ + H_2 \rightarrow NADH + H^+$. This additional production of hydrogen ions may also be seen as an additional benefit in that reduction of carbon dioxide to methanol consumes three hydrogen ions per carbon dioxide molecule.

Other techniques for supplying additional electrons and hydrogen ions will also be readily apparent. For example, electrons can be produced electrochemically, electrolytic processes may be used to produce the hydrogen ions from the water as well as electrons, electroactive sol-gels may be produced by doping with metals or electrically conductive polymers, or photoactive inorganic components such as titanium oxide may be employed.

Contacting the Enzymne-Containing Matrix with Carbon Dioxide

In a preferred embodiment, a sol-gel matrix is prepared as described in Enzymatic Conversion of Carbon Dioxide to Methanol: Enhanced Methanol Production in Silica Sol-Gel Matrices, R. Obert and B. Davé (the inventor herein), J. Am. Chem. Soc. 1999, 121, 12192–12193. In summary, the gel may be prepared by mixing tetramethoxysilane precursor, water and HCl to form a mixture that is then sonicated to form a sol. The sol is added to a stock of the combination of enzymes described above in buffer (pH 7) and if the NADH is to be regenerated by means of a PSII system, a suspension of PSII particles are added to the sol. Where NADH is used as the terminal electron and hydrogen donor, the resulting gel is allowed to age and immersed in a solution of NADH to allow the NADH molecules to diffuse into the gel. The resulting gel containing the three enzymes of this invention, the NADH and the PSII system may be crushed to a particulate or powder form and maintained in suspension in water held in a reaction vessel such as a CSTR.

Carbon dioxide, such as atmospheric carbon dioxide, may be bubbled under constant positive pressure through the water and so diffused through the matrix and contacted with the enzymes entrapped in the matrix. Remaining carbon dioxide and resulting methanol then diffuse out of the matrix and through the water for collection by distillation and the recirculation of the aqueous fraction, if so desired.

The following examples describe preferred embodiments of the invention. Other embodiments with the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

Enzymatic conversion of carbon dioxide to methanol was attempted in solution phase with an enzyme stock solution comprising 10 mg/mL of each of the formate, formaldehyde and alcohol dehydrogenase enzymes dissolved in 0.1 M phosphate buffer at pH 7. Reaction mixtures were prepared by adding 1.0 mL of the enzyme stock solution to 1.0 mL of various concentrations of NADH solution in polystyrene cuvettes such that the final concentration of NADH in the cuvettes varied from 0.025 to 0.1 M. The cuvettes were covered with Parafilm to prevent extensive loss of methanol-formed by evaporation, and gaseous $CO_2$ was then bubbled through this solution for 3 hours using a small nozzle with an outlet diameter of about 0.5 mm and through a hole in the Parafilm. The extended time of bubbling of $CO_2$ ensured that the reaction was allowed to go to completion and that equilibrium was established. Quantitative measurement of methanol was carried out with gas chromatography (GC). A calibration curve was established for aqueous methanolic solutions with known concentrations of methanol ranging from 0.001 to 0.05 M. To evaluate the concentration of methanol produced as a result of the enzyme-catalyzed reaction, 1.0 µL of the final reaction solution was used for GC measurements. The concentration of methanol was calculated by using peak areas for the characteristic methanol band in the chromatogram. The results are shown in Table 1, below. The amount of each enzyme in solution was 5 mg. Because the NADH was the limiting reagent in the reaction, the methanol yield and so efficiency of the reaction are given relative to the amount of NADH used. As is clear from the reaction shown in FIG. 1, three moles of NADH are consumed for each mole of methanol produced. Thus, a 100% yield of methanol corresponds to one mole of methanol produced for every three moles of NADH employed.

TABLE 1

| NADH (µmoles) | Methanol (µmoles) | Methanol/ NADH | % Yield |
|---|---|---|---|
| 50 | 1.3 ± 0.7 | 0.02 | 7.8 |
| 100 | 7.0 ± 0.9 | 0.07 | 21.0 |
| 150 | 10.2 ± 0.6 | 0.07 | 20.4 |
| 200 | 11.2 ± 0.9 | 0.05 | 16.8 |

EXAMPLE 2

Enzymatic conversion of carbon dioxide to methanol was carried out in a sol-gel glass. Sol-gel encapsulated samples were prepared by the biocompatible synthesis method reported by Ellerby et al., in Science 255, 1113 (1992). Tetramethoxysilane (TMOS) was used as a precursor for making the silica sol-gel. The initial sol-gel was prepared by mixing TMOS (3.82 g), water (0.85 g) and 0.04 M HCl (0.055 g). The mixture then was sonicated for 20 minutes to form sol. Each of several gels was prepared by adding 1.0 mL of the enzyme stock solution of Example 1, above, to 1.0 mL of the sol in a polystyrene cuvette. Typical gelation times were about ten to thirty seconds. Each cuvette then was covered with Parafilm and the gel was allowed to age at 4° C. for 24 hours. To ensure complete removal of methanol generated due to hydrolysis of TMOS during the sol-gel process, after the initial aging process the gels shrunk, were removed from the cuvettes, and were transferred to beakers, each of which contained 250 mL of 0.1 M phosphate buffer at pH 7. The beakers were placed in a refrigerator at 4° C. for 24 hours. The gels were transferred to new 250-ml beakers containing fresh 0.1 M phosphate buffer at pH 7, which were then placed in the refrigerator for another 24 hours. This step was repeated; that is, the gels again were transferred to new 250-ml beakers containing fresh 0.1 M phosphate buffer at pH 7, which were then placed in the refrigerator for another 24 hours, for a total of 72 hours of soaking in the buffer bath.

After the initial equilibration, the gels were transferred to standard polystyrene cuvettes followed by addition of 1.0 mL of various concentrations of NADH solution in polystyrene cuvettes such that the final concentration of NADH in the cuvettes varied from 0.025 to 0.1 M. To allow the NADH to diffuse into the gels, the samples containing the gels and the NADH solution were left undisturbed for 48 hours. Carbon dioxide then was bubbled through the mixtures for three hours for production of methanol. The concentration of methanol produced was determined for each sample using GC by taking a 1.0 µL aliquot of the solution. The results are shown in Table 2, below, along with the results from Example 1, above. The amount of each enzyme in the sol-gel was 5 mg. As with Example 1, above, the NADH was the limiting reagent in the reaction, and so the methanol yield and efficiency of the reaction are given relative to the amount of NADH used. As also explained in Example 1, above, the yield is based on a 100% yield of methanol corresponding to one mole of methanol produced for every three moles of NADH employed.

TABLE 2

| NADH (µmoles) | Methanol (µmoles) | Methanol/ NADH | % Yield |
|---|---|---|---|
| 50 | 15.2 ± 0.4 | 0.30 | 91.2 |
| 100 | 26.6 ± 0.6 | 0.26 | 79.8 |
| 150 | 28.5 ± 0.7 | 0.19 | 57.0 |
| 200 | 29.2 ± 0.6 | 0.15 | 43.8 |

EXAMPLE 3

Sol-gels were prepared according to the method of Example 2, above, except that a suspension of PSII particles (0.5. mL) derived from green spinach were also added to the sols. Also as in Example 2, the gels were equilibrated with copious amounts of phosphate buffer (pH 7) to removal any residual methanol from the gels and were immersed in a solution of NADH to allow NADH molecules to diffuse into the gels. The gels were crushed to a powder, which was then suspended in water containing NADH. The system was irradiated with a tungsten lamp and generation of methanol was monitored by bubbling carbon dioxide through the mixture for 3 to 4 hours, after which an aliquot of the liquid was taken for measurement of the methanol peak by GC. The methanol production yield was substantially larger than that achieved by the process of Example 2, which did not contain the PSII particles. In fact, while the yield of the process of Example 2 approached 100% based on NADH consumption, the yield of methanol for the process containing the PSII particles was on the order of 300,000%, suggesting continuous and repeated regeneration of the NADH.

All references, including without limitation all papers, publications, presentations, texts, reports, manuscripts, brochures, internet postings, journal articles, periodicals, and the like, cited in this specification are hereby incorporated by reference. The discussion of the references herein is intended merely to summarize the assertions made by their authors and no admission is made that any reference constitutes prior art. The inventors reserve the right to challenge the accuracy and pertinence of the cited references.

In view of the above, it will be seen that the several advantages of the invention are achieved and other advantageous results obtained.

As various changes could be made in the above methods and compositions without departing from the scope of the invention, it is intended that all matter contained in the above description as shown in the accompanying drawings shall be interpreted as illustrative and not in a limiting sense.

What is claimed is:

1. A method for conversion of carbon dioxide to methanol comprising contacting formate dehydrogenase enzymes, formaldehyde dehydrogenase enzymes and alcohol dehydrogenase enzymes with the carbon dioxide in the presence of a terminal electron donor to produce the methanol.

2. A method as set forth in claim 1 wherein the additional dehydrogenase enzymes are methanol dehydrogenase enzymes.

3. A method as set forth in claim 1 wherein the alcohol dehydrogenase enzymes are other than methanol dehydrogenase enzymes.

4. A method as set forth in claim 1 wherein the formate dehydrogenase, formaldehyde dehydrogenase and alcohol dehydrogenase enzymes are fixed in a microporous matrix.

5. A method as set forth in claim 4 wherein the microporous matrix is a sol-gel matrix.

6. A method as set forth in claim 1 wherein the terminal electron donor is reduced nicotinamide adenine dinucleotide.

7. A method as set forth in claim 5 wherein the terminal electron donor is reduced nicotinamide adenine dinucleotide.

8. A method as set forth in claim 6 wherein the reduced nicotinamide adenine dinucleotide is oxidized to nicotinamide adenine dinucleotide upon donation of a terminal electron and is regenerated back to reduced nicotinamide adenine dinucleotide to serve again as a terminal electron donor.

9. A method as set forth in claim 7 wherein the reduced nicotinamide adenine dinucleotide is oxidized to nicotinamide adenine dinucleotide upon donation of a terminal electron and is regenerated back to reduced nicotinamide adenine dinucleotide to serve again as a terminal electron donor.

10. A method as set forth in claim 8 wherein the reduction of the carbon dioxide to methanol takes place in water and the reduced nicotinamide adenine dinucleotide is regenerated by a photosystem preparation exposed to light.

11. A method as set forth in claim 9 wherein the reduction of the carbon dioxide to methanol takes place in water and the reduced nicotinamide adenine dinucleotide is regenerated by a photosystem preparation exposed to light.

12. A method as set forth in claim 10 wherein the photosystem preparation is a photosystem II preparation.

13. A method as set forth in claim 11 wherein the photosystem preparation is a photosystem II preparation.

14. A method as set forth in claim 8 wherein the nicotinamide adenine dinucleotide is regenerated back to reduced nicotinamide adenine dinucleotide by contacting the nicotinamide adenine dinucleotide with hydrogen.

15. A method as set forth in claim 9 wherein the nicotinamide adenine dinucleotide is regenerated back to reduced nicotinamide adenine dinucleotide by contacting the nicotinamide adenine dinucleotide with hydrogen.

16. A method as set forth in claim 9 wherein the sol-gel matrix is electroactive and the sol-gel matrix regenerates the reduced nicotinamide adenine dinucleotide from the nicotinamide adenine dinucleotide.

17. A method for reduction of formaldehyde to methanol by alcohol dehydrogenase catalysis, comprising exposing alcohol dehydrogenase enzymes retained in a microporous matrix to the formaldehyde.

18. A method as set forth in claim 17 wherein the formaldehyde is produced by reduction of formate to the formaldehyde by formaldehyde dehydrogenase catalysis, comprising exposing formaldehyde dehydrogenase enzymes retained in a microporous matrix to the formate.

19. A method as set forth in claim 18 wherein the formate is produced by reduction of carbon dioxide to the formate by formate dehydrogenase catalysis, comprising exposing formate dehydrogenase enzymes retained in a microporous matrix to the carbon dioxide.

20. A method as set forth in claim 17 wherein reduced nicotinamide adenine dinucleotide acts as a terminal electron donor in the reduction.

21. A method as set forth in claim 18 wherein reduced nicotinamide adenine dinucleotide acts as a terminal electron donor in each of the reductions.

22. A method as set forth in claim 19 wherein reduced nicotinamide adenine dinucleotide acts as a terminal electron donor in each of the reductions.

23. A method as set forth in claim 22 wherein the reduced nicotinamide adenine dinucleotide is oxidized to nicotinamide adenine dinucleotide upon donation of terminal electron to the reductions and is regenerated back to reduced nicotinamide adenine dinucleotide to serve again as a terminal electron donor for further reduction reactions.

24. A method as set forth in claim 2 wherein the formate dehydrogenase, formaldehyde dehydrogenase and alcohol dehydrogenase enzymes are fixed in a microporous matrix.

\* \* \* \* \*